United States Patent [19]

Liu et al.

[11] Patent Number: 4,571,292

[45] Date of Patent: Feb. 18, 1986

[54] APPARATUS FOR ELECTROCHEMICAL MEASUREMENTS

[75] Inventors: Chung-Chiun Liu; Vasilios A. Karagounis, both of Cleveland Heights, Ohio

[73] Assignee: Case Western Reserve University, Cleveland, Ohio

[21] Appl. No.: 407,566

[22] Filed: Aug. 12, 1982

[51] Int. Cl.⁴ .................................... G01N 27/46
[52] U.S. Cl. ............................ 204/412; 204/415; 204/1 T; 427/123; 427/125; 128/635
[58] Field of Search ......................... 204/412, 415; 427/123–125

[56] References Cited

U.S. PATENT DOCUMENTS

| | | | |
|---|---|---|---|
| 3,260,656 | 7/1966 | Ross | 204/415 |
| 3,719,564 | 3/1973 | Lilly et al. | 204/426 |
| 3,776,832 | 12/1973 | Oswin et al. | 204/1 K |
| 4,076,596 | 2/1978 | Connery et al. | 204/415 |
| 4,100,048 | 7/1978 | Pompei et al. | 204/415 |
| 4,172,770 | 10/1979 | Semersky et al. | 204/412 |
| 4,324,257 | 4/1982 | Albard et al. | 204/412 |
| 4,450,842 | 5/1984 | Zick et al. | 204/415 |

FOREIGN PATENT DOCUMENTS 2073891 10/1981 United Kingdom .............. 204/415

Primary Examiner—T. Tung
Attorney, Agent, or Firm—Renner, Otto, Boisselle & Lyon

[57] ABSTRACT

A sensor for an electrochemically active species, such as oxygen, uses more than two electrodes, namely, at least a working electrode, counter electrode and reference electrode. The sensor preferably is substantially planar, is made using thick film or thin film technique and accordingly may be very small. With the sensor in an electrolyte balanced reverse reactions occur, respectively, at the working and counter electrodes while no reaction occurs at the reference electrode, which is maintained in equilibrium with the electrolyte, and voltage between the working the reference electrodes is maintained constant. Current flow between the working and counter electrodes, then, provides an accurate, stable representation of species concentration.

32 Claims, 10 Drawing Figures

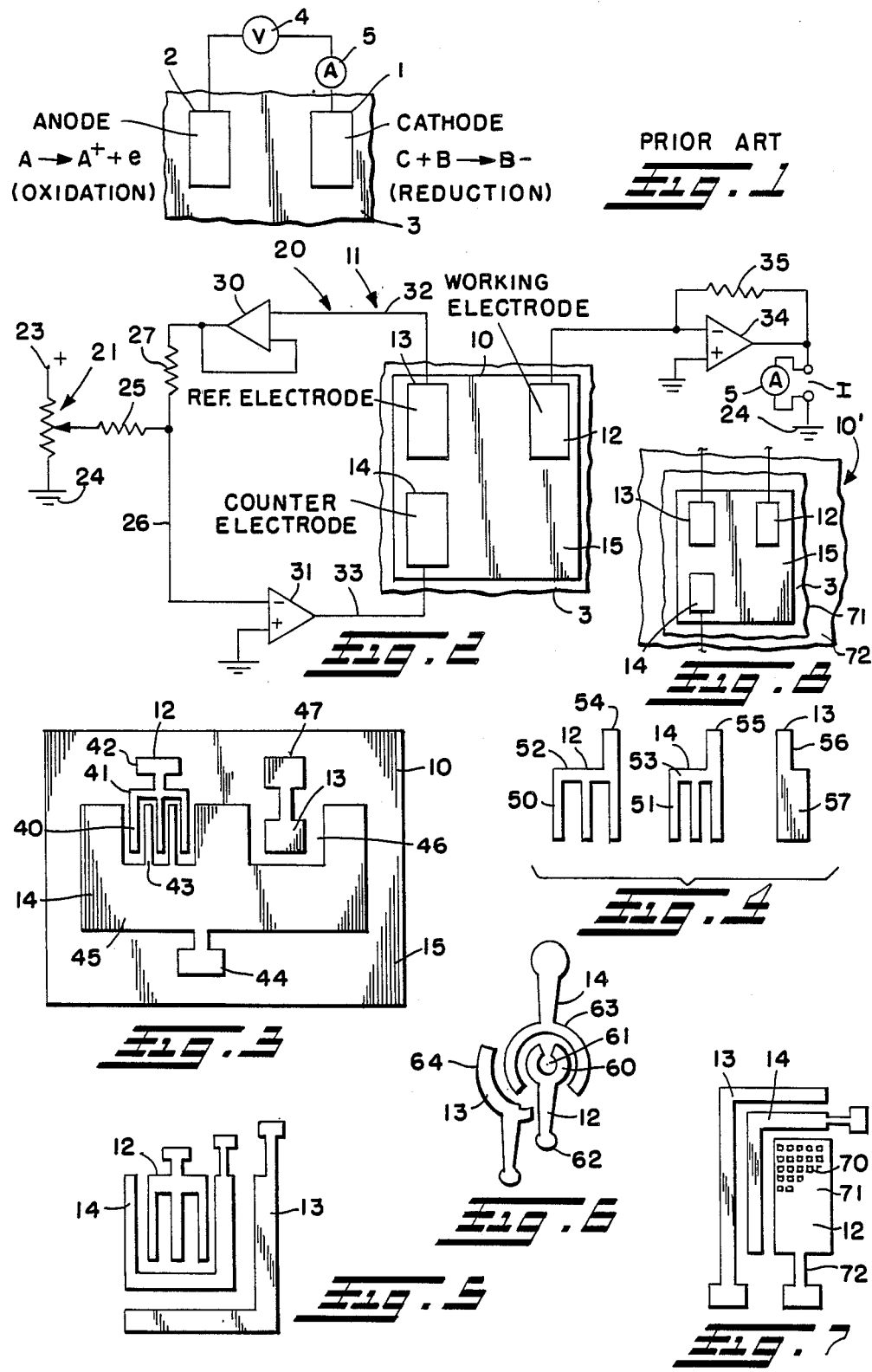

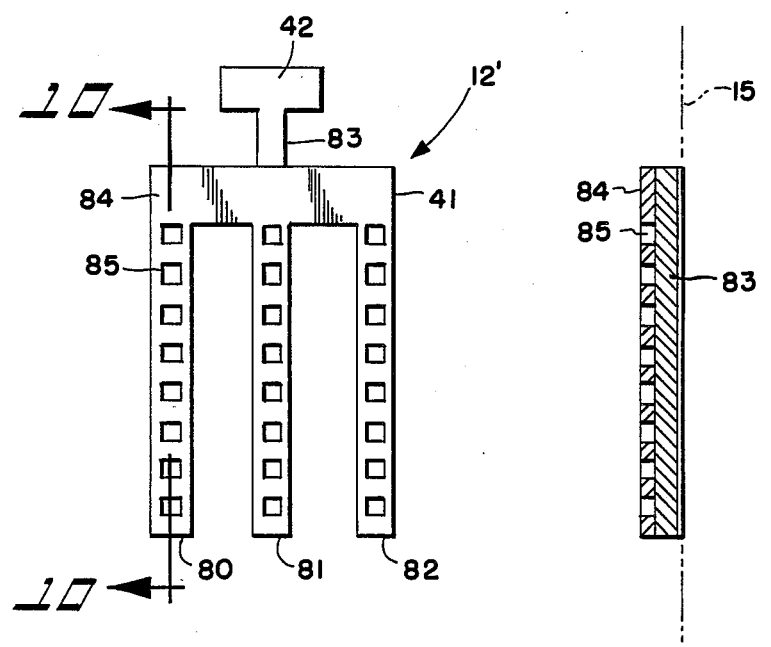

APPARATUS FOR ELECTROCHEMICAL MEASUREMENTS

TECHNICAL FIELD

The present invention relates generally, as indicated, to apparatus and method for electrochemical measurements and, more particularly, to electrochemical measurements of certain species, especially of the type that undergo oxidation and/or reduction reactions, and/or other types of reactions.

BACKGROUND OF PRIOR ART

In U.S. Pat. Nos. 3,260,656 and 4,076,596 is presented information concerning principles of operation of prior art sensors, detectors, methods, etc. for detecting the concentration in fluids of an electrochemically active species. The entire disclosures of such patents hereby are incorporated by reference. As used in such patents and herein "fluids" includes gases, liquids, vapors, mixtures thereof, and virtually any other material in which an electrochemically active species may occur and/or be detected.

For example, in the past, detection of the concentration of oxygen as an electrochemically active species in a material was performed by measuring current flow developed by oxidation or reduction reactions. The present invention contemplates such oxygen concentration detection and also detection of other electrochemically active materials by oxidation of reduction current generated technique and/or other reactions that generate an electrical parameter that can be measured, such as current or voltage. Primarily, though, electrochemically active species ordinarily means any group of identical chemical entities, such as ions, molecules, atoms, etc., which are capable of being separated by electrochemical type reaction, such as oxidation or reduction, or other reaction, to yield an electrical parameter, such as current or voltage, that may be detected as a representation of the concentration, for example, of such species.

A conventional approach to measuring oxygen concentration has been to place two electrodes 1, 2 (as seen in FIG. 1), one a working electrode (the cathode, for example of gold, platinum or other noble metal or carbon) and the other a reference electrode (the anode, for example of silver, silver-silver chloride or other material), in an electrolyte 3 having the species, the concentration of which is to be measured. A voltage from source 4 is applied across the electrodes causing a reduction reaction at the cathode, an oxidation reaction at the anode, while maintaining a charge balance in the electrolyte. Exemplary equations for the reduction and oxidation reactions are shown, respectively in equations 1 and 2 below.

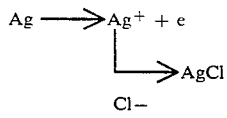

(1)

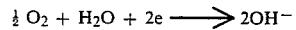

$$\tfrac{1}{2} O_2 + H_2O + 2e \longrightarrow 2OH^-$$ (2)

The current flowing between the electrodes 1, 2 would result from the reactions occurring in the electrolyte; and such current would have a proportional relationship to the concentration of the electrochemically active species and could be measured by a meter 5. Such method is disclosed, for example, in the above mentioned patents.

More specifically, in the '656 patent the cathode and anode, for example of noble metal, are placed in an electrolyte of potassium hydroxide, the combination being within a selectively permeable barrier or membrane that permits passage only of the electrochemically active species therethrough. In such patent the cathode is solid material and the anode is mesh material; and those types of electrodes may be used also in the present invention. Use of gold, platinum, silver, silver oxide, silver-silver chloride electrode materials are mentioned. The patentee also describes the possible problem of pH changes due to consumption of $H^+$ and suggests adding a buffer for prolonged operation. The '656 patent further shows a three electrode package, including a so-called consuming electrode cathode, an anode, and a reference electrode, and an energization circuit using an amplifier to apply a voltage between the cathode and reference electrodes while the potential of the reference electrode is fixed at a virtual ground.

In the '596 patent there is disclosed a technique for placing an anode and cathode of an oxygen sensor on an electrically non-conductive, inert, for example, plastic, material substrate using a thick film technique and/or a thin film technique. Sputtering and/or evaporation is used to deposit a thin film of metal on the substrate to form the electrode surfaces. Definition of the surface areas is achieved by photo-etching. Use of a further separate reference electrode like the third electrode shown in the '656 patent, also is mentioned. U.S. Pat. No. 4,062,750 is another example of thin film technique used to form an electrochemical electrode and cell.

A number of problems have been encountered in the aforementioned types of electrochemically active species sensors. These include inaccuracies caused by measuring the current flow resulting from the reactions occurring at both the working and reference electrodes and caused by changes encountered as the reference electrode material itself is consumed as well as inaccuracies due to the effect of IR voltage drop in the electrolyte between the two electrodes. For example, the current flow between the two electrodes when a voltage is applied thereacross would be a function of the reduction and oxidation reactions occurring, respectively, simultaneously at the electrodes; whereas only one of those reactions directly proportionally represents species concentration. Therefore, in the past the current density at the reference electrode has been minimized while the relative current density at the working electrode has been increased by relying on a convention to size the electrodes such that the reference electrode has about fifty times the surface area of the working electrode. This size relationship has been beneficial in reducing, although not eliminating, the relative affect on the measured current of current due to the forced reaction occurring at the reference electrode and in intensifying the affect on or proportion of the measured current of current due to the reduction reaction, for example, occurring at the working electrode. Such size relationship also results in the reference electrode itself being so large that small consumption thereof would not detrimentally affect operation of the sensor; therefore, sensor longevity and accuracy during life will be improved over a sensor with about equal size electrodes.

Unfortunately, the just mentioned fifty to one size convention creates a restriction on the miniaturization possibility for the sensor. Yet, it is desirable to provide such sensors of a variety of sizes, from rather large to measure electrochemically active species, for example in commercial or industrial processes, to rather small sensors, for example for biomedical purposes.

SUMMARY OF THE INVENTION

Briefly, in accordance with the present invention an electrochemical sensor and system employs more than two electrodes, including, in particular, a working electrode, a reference electrode and a counter electrode. The sensor preferably is made using thick film and/or thin film technique, especially by deposition of multiple electrodes on a flexible polymeric substrate. Therefore, the sensor may be substantially planar and capable of substantial miniaturization while still having relatively fast, accurate and stable response. Thus, the sensor is particularly useful for intravivo measurements, even including sensor implantation techniques.

The system employs a stable energization source that maintains a substantially constant voltage relationship between the working electrode and reference electrode by a feedback control that includes the relationship of the reference electrode/counter electrode voltage. Moreover, the chemical reactions occurring as a result of such electrode energization in the system does not include a reaction at the reference electrode. Current measurement is prompt, accurate and stable, being a function proportional to concentration of the electrochemically active species intended for detection; such measured current is that current flowing between the counter electrode and working electrode. Consumption of the reference electrode will not occur and will not detrimentally influence accuracy of the current flow measurements; since no reaction is occurring at the reference electrode, which is at equilibrium with the electrolyte, there will be no extra current generated there that would detrimentally influence accuracy of the desired current flow measurements; and the fifty to one relationship in surface areas of the reference electrode to the working electrode no longer is necessary. Again, as a result of the latter, in particular, the sensor may be substantially miniaturized.

With the foregoing and following description in mind, a primary object of the present invention is to improve the accuracy and stability, especially over long periods, of measurement of concentration of electrochemically active species in materials.

Another object is to provide improvements in an electrode sensor using more than two electrodes for electrochemical measurements.

An additional object is to provide improvements in apparatus and methods for electrochemical measurements.

A further object is to maintain a constant voltage between a working electrode and reference electrode in an electrochemical measuring system, especially by monitoring and/or controlling voltage relationship between reference and counter electrodes.

Still another object is to effect electrochemical measurements without consuming a reference electrode.

Still an additional object is to reduce the size requirement for electrodes used in an electrochemical sensor and system employing the same.

Still a further object is to permit and facilitate intravivo electrochemical measurements, for example, measurements of oxygen concentration in blood flowing through the body.

Even another object is to miniaturize a sensor for an electrochemically active species.

Even an additional object is to facilitate combining other sensors with an electrochemically active species sensor.

In accordance with one aspect of the present invention a sensor for an electrochemically active species includes a substrate, a working electrode supported by said substrate, a reference electrode supported by said substrate, and a counter electrode supported by said substrate. Another aspect relates to use of such sensor with an electrical source/circuit to energize the sensor and to measure species concentration.

According to an additional aspect of the invention a method of making a sensor for use in sensing electrochemically active species in an electrolyte includes using a thick film or thin film deposition method applying at least three electrically isolated electrodes to a substrate.

According to a further aspect of the invention, a method of measuring concentration of an electrochemically active species includes energizing a sensor having at least a working electrode, a reference electrode, and a counter electrode to cause reactions at said working and counter electrodes, and measuring an electrical property related to the reaction at the working electrode as a representation of such concentration. Another aspect concerns relying on an equilibrium condition of the reference electrode to set voltage level.

These and other objects and advantages of the present invention will become more apparent as the following description proceeds.

To the accomplishment of the foregoing and related ends, the invention, then, comprises the features hereinafter fully described in the specification and particularly pointed out in the claims, the following description and the annexed drawing setting forth in detail certain illustrative embodiments of the invention, these being indicative, however, of but several of the various ways in which the principles of the invention may be employed.

BRIEF DESCRIPTION OF THE DRAWING

In the annexed drawing:

FIG. 1 is a schematic view of a prior art two electrode electrochemical sensor system;

FIG. 2 is a schematic illustration of the electrochemical sensor and system in accordance with the present invention employing a working electrode, reference electrode, and counter electrode;

FIGS. 3 through 7 are schematic illustrations of several types of electrode configurations in accordance with the invention;

FIG. 8 is a schematic illustration of the electrochemical sensor employing a selectively permeable barrier; and FIGS. 9 and 10, respectively, are plan and partial section view of a preferred electrode configuration.

DESCRIPTION OF THE PREFERRED EMBODIMENT

Referring now in detail to the drawing, wherein like reference numerals designate like parts in the several figures, and intially to FIG. 1, a prior art electrochemical sensor system is shown. Such system includes two electrodes 1, 2 in an electrolyte 3. Electrical leads connect the voltage source 4 to the electrodes. A reduction reaction occurs at the cathode or working electrode 1, and an oxidation reaction occurs at the anode or reference electrode 2. Due to such reactions, an electrical current will flow between the cathode and the anode. That electrical current may be measured by a conventional meter 5 as a representation of the concentration of the electrochemically active species, such as oxygen, in the electrolyte. An exemplary oxidation reaction of equation 1 above shows silver of a silver or silver-silver chloride anode 2 yielding a silver ion plus an electron; and in the presence of a chlorine ion the silver ion and chlorine ion form silver chloride. The exemplary reduction reaction in which the cathode 1 may be, for example, gold, platinum or other noble metal, shows the combination of oxygen and water molecules plus three electrons to yield hydroxyl radicals. The oxidation and reduction reactions must be charge balanced, but, as is quite clear from equations 1 and 2, and is well known in the art, such oxidation and reduction reactions usually are not reverse or opposite ones. Therefore, as was mentioned above, it is common to encounter consumption of the reference electrode in particular, and such consumption can have a detrimental affect on accuracy and stability, especially over a long time, of the prior art sensor and system in which it is used.

Turning specifically to FIG. 2, now, an improved sensor 10, in accordance with the present invention, used in a sensor system 11 is shown in detail. The fundamental components of the sensor 10 include at least three electrodes, specifically a working electrode 12, a reference electrode 13, and a counter electrode 14, preferably all formed by thick film or thin film deposition technique on a common base or substrate 15. The sensor 10 may be planar, may be comprised of multiple parallel connected electrodes for response speed and accuracy, and may be substantially miniaturized. The sensor system 11 includes the sensor 10 and an electrical circuit 20 which energizes the sensor and detects current flow, in the manner to be described in greater detail below.

It is the purpose of the circuit 20 to energize the electrodes of the sensor 10 to maintain a constant voltage between the working electrode 12 and reference electrode 13, even though temperature, pH, and/or other parameters may vary. The circuit 20 also, preferably in cooperation with the materials of which the electrodes are formed and the electrolyte and species material(s), energizes the sensor 10 to cause balanced reverse reactions to occur, respectively, at the working electrode 12 and counter electrode 14 and no reaction to occur at the reference electrode 13 when the sensor 10 is in an electrolyte 3. Such reactions would be, for example, as follows:

At the working electrode is, for example, the following reduction reaction

(3)

At the counter electrode is the following oxidation reaction

(4)

Due to the total reversibility of the reactions occurring at the working and counter electrodes and no reaction occurring at the reference electrode, there will be maintained a charge balance in the electrolyte and there will not be any substantial consumption, preferably none at all, of the respective electrodes. Moreover, since reactions are totally reverse of each other, the reaction occurring at the counter electrode does not affect measurement of current flowing at the working electrode 12 as is measured by the meter 5. Since no reaction occurs at the reference electrode 13 and it is in equilibrium with the electrolyte the current produced at the working electrode is due only to the oxidation or reduction reaction at the working electrode. Such current is directly proportional to species concentration. Further, since the electrodes are not consumed, prior consumption detrimentally affecting current measurements is eliminated. Accordingly, the sensor 10 and use thereof in a system 11 will provide a highly stable accurate measurement of concentration of an electrochemically active species, such as oxygen, even over long periods of time.

Furthermore, since the reactions occurring at the working and counter electrodes 12, 14 are balanced and reverse, there is no forced reaction; and this together with the non-consumption of the electrodes eliminates the need for the fifty to one surface area ratio of reference to working electrode convention of the prior art electrochemical sensor technology.

Contributing further to the accuracy and stability of measurements made using a sensor in accordance with the invention, is the ability to form and actual formation of especially the working electrode 12, and, if desired, the other electrodes, in a multiple parallel connected electrode configuration. Each electrode portion of the working electrode may be quite small so as to have a rapid response; and although each electrode portion is small and, thus, results in only a small current flow contribution, the parallel arrangement of such electrode portions enables the sum of such individual small currents to be measured. Such sum is relatively large and, therefore, results in improved signal-to-noise ratio and, therefore, sensor/measurement accuracy, even in a miniature sensor.

Since a sensor 10 in accordance with the present invention would not require such fifty to one surface area ratio, it is possible, now, for each of the electrodes 12, 13, 14 to be substantially the same size and, in particular, to be rather small. For example, using available technology relating to thick film and thin film techniques, the electrodes 12, 13, 14 may be deposited on a substrate 15 that is of a size on the order of about ten microns by about ten microns. Sizes mentioned herein are surface area sizes for substrates or the like that have, for example, two orthogonal directions, being at least approximately rectangular in shape. Such shape is not essential to the invention, though. The size ranges may be applicable to other shapes of substrates and the like in accordance with the present invention. It is believed that technology is or soon also will be available enabling a sensor 10 to be made in the so-called micron size range. Without being restricted by the prior fifty to one size requirement and achieving the relatively high accuracy and stability of the sensor 10 in accordance with the present invention, such sensor has substantial utility in biomedical application, including in particular intravivo measurements.

Such a small sensor 10, especially when employing a flexible polymeric substrate, could be used, for example, by implantation in the body of a person to measure, for example, oxygen concentration in the blood or or tissue even at the skin, the latter relying on additional techniques of using, for example, conductive gel or polymeric material as an electrolyte at the skin surface. A sensor 10 according to the present invention also may be used in other biomedical types of applications, including, for example, urea measurements. A sensor 10 according to the invention may be used, too, in environmental applications, oceanography, and industrial or commercial process monitoring and/or control. As an example of the latter, fermentation may be monitored and controlled.

As an added dimension to the present invention, due importantly to the stability of information obtained from the sensor 10 and system 11, additional tranducers/sensors may be employed with the sensor 10, including mounting of the same on the substrate 15, for example. Such additional sensors may be, for example, temperature sensors, pH sensors, conductivity sensors, and so on. Such inclusion may be effected without detrimentally affecting the accurate electrochemically active species concentration information obtained using the sensor 10.

Moreover, a sensor 10 according to the present invention may be employed as a bare sensor placed in an electrolyte and, just as well, can be used with a selectively permeable membrane in an approach of the type, for example, disclosed in the above mentioned patents. The sensor 10 and system 11 also may be used in water containing electrolyte, such as ethylene glycol/water mixture, and, as was mentioned above, even directly in a conductive gel or polymeric type electrolyte.

The substrate 15 may be formed of plastic, glass, ceramic, alumina, quartz, or any other material that preferably is inert, or at least inert relative to the material of which the electrodes are formed and the material into which the sensor 10 is intended to be placed for use. Preferably the substrate is a flexible polymeric material. When used for biomedical purposes, such as to sense oxygen concentration, the substrate 15, indeed the entire sensor 10, preferably is disposable. The substrate may be made as small as possible, being of a size adequate to support thereon the required at least three electrodes 12, 13, 14 to function in the manner described herein. Using current thick or thin film technology for applying the electrodes to the substrate, such substrate, and, accordingly, the sensor 10 may be small enough, say in the square millimeter size range, to place the same for use on the tip of a medical catheter. In the preferred embodiment, the shape of the substrate 15 is rectangular, although such shape may be other than rectangular, as is desired. Also, although the substrate 15 preferably is substantially flat or curved, but nevertheless relatively larger in the two illustrated surface area dimensions/directions than thickness dimension, the substrate and the electrodes 12, 13, 14 may be made in cylindrical or other format, such as the cylindrical format shown in the above mentioned '596 patent. The size of the sensor 10 may be substantially greater than the square micron or square millimeter size ranges described herein as useful particularly in biomedical applications; for example, for oceanographic, environmental, commercial and/or industrial purposes, the substrate size, and that of the sensor 10 as a whole, may be substantially greater, as space and other environmental and/or electrochemical conditions dictate.

Using the thick or thin film technique for applying the electrode material to the substrate 15, accurately defined electrodes may be formed. Moreover, the size of such electrodes may be quite small and impurities may be minimized due to deposition in a controlled environment.

Preferably the working electrode 12 and the counter electrode 14 are formed of the same material, although this is not a requirement. Such material, though, preferably is inert relative to the substrate and the electrolyte as well as to the electrochemically active species intended to be detected. Thus, such material may be selected from the group of noble metals. A preferred material of which the working electrode is formed may be selected from the group including gold, platinum, silver, and carbon. Likewise, the counter electrode should be of such material. A particular advantage to having a working electrode 12 and counter electrode 14 formed of the same material is to assure that the reactions occurring there will be substantially totally balanced and reverse of each other. An important advantage of the present invention in which substantially completely reverse reactions occur at the working and counter electrodes 12, 14, is that there need not be any concern for consumption of oxygen or other electrochemiccally active species, by such reactions. In contrast, though, the above-mentioned patents are directed to improvements in such electrochemically active species detectors that do not necessarily consume the electrochemically active species itself.

Alternatively, the counter electrode 14 may be formed of a material other than that of which the working electrode 12 is formed. For example, counter electrode 14 may be of silver-silver chloride. In such event, rather than encountering the reaction noted above in equation 4 at the counter electrode 14, a reaction of the type in equation 1 may be encountered. Such reaction would not be the true reverse reaction of that occurring at the working electrode 12, and, therefore, the accuracy and stability of a sensor 10 in which the counter electrode material and the working electrode material are different would probably not be as great as that when such materials are the same or at least substantially the same. However, using the working, reference and counter electrode arrangement of the sensor 10 according to the present invention, even though the materials of which the counter and working electrodes are formed would be different from each other, would provide a more accurate and stable measurement of electrochemically active species concentration than in the prior art two electrode system because of the accurate maintenance of constant voltage between the working and reference electrodes in the present invention and preferably the minimization, if not exclusion, of reaction at the reference electrode.

The materials of which the reference electrode may be formed, include, for example, silver-silver chloride, mercuric-mercuric chloride (Calomel), and other known, and perhaps unknown, materials. The same is true, too, for selecting of the materials for the working electrode and counter electrode; such materials should have the desired inert property, electrically conductive property, and/or other properties needed for appropriate operation of the sensor 10.

In FIG. 2 the circuit 20 portion of the sensor system 11 includes a voltage source 21 formed by an adjustable potentiometer 22 across which the positive and ground terminals 23, 24, respectively, of a DC voltage supply are connected. From the wiper contact of the potentiometer 22 the voltage is coupled by a resistor 25 to line 26 and resistor 27. Operational amplifiers 30, 31, which have appropriate voltage inputs, not shown, are connected, respectively, by lines 32, 33 to the reference electrode 13 and counter electrode 14. The circuit 20 also includes a further amplifier 34 with a feedback resistor 35 connected between the working electrode 12 and, via the meter 5, the ground terminal 24. Voltage connections for the amplifier 34 also are provided but are not shown in FIG. 2. It is the purpose of the circuit 20, and particularly of the amplifiers 30, 31, to provide appropriate feedback relation between the reference electrode and voltage source 21, and counter electrode 14 such that as various environmental and/or other parameters may vary in the electrolyte 3, the voltage applied by the source 21 in particular across the working electrode 12 and reference electrode 13 will be maintained constant.

More particularly, the reference electrode 13 is at equilibrium with the electrolyte 3 at the interface therebetween. Amplifier 30 feeds back the potential of the reference electrode 13 to the input of amplifier 31, which, in turn, provides voltage input to the counter electrode. This circuit arrangement, therefore, relies on the reference electrode 13 to set the voltage level. Accordingly, the potential between the reference electrode 13 and working electrode 12 is fixed; and, therefore the potential between the working electrode 12 and the electrolyte is fixed.

Current flow at the working electrode 12, the, may be measured accurately by the meter 5. Such current is due to the reduction occurring at the working electrode 12 and, therefore, represents accurately concentration of the chemically active species. The amplifier 34 provides appropriate gain and/or impedance requirements for accurate current measurements. Also, since the meter 5 is connected at one sside to a ground reference, the stability of current measurements thereby will be enhanced.

Although the three electrode arrangement of the present invention is particularly useful for examining an electrochemically active species in an oxidation and/or reduction reaction, whereby the meter 5 measures current flow as a representation of species concentration, the analog also may be true. Specifically, means may be provided such that current excitation is provided for the sensor 10 and it is voltage relationship that would be measured. Moreover, the sensor 10 may be used in detecting a species concentration with reactions other than those of the oxidation and/or reduction type, such as, for example, urea reactions.

In FIG. 3 is shown a preferred embodiment and best mode of the sensor 10 in accordance with the present invention. In the embodiment in FIG. 3 the substrate 15 is formed of plastic material and is of a size on the order of about one millimeter by about 1.5 millimeters. The working electrode 12 is of the prong-like fork shape having several prongs 40 extending from a common base 41 and a terminal pad 42 connected to the base. The terminal pad provides a place for attaching an electrical lead to the electrode 12. The counter electrode 14 has a number of fork-like portions 43 that extend in an interdigitated arrangement relative to the prongs 40 of the working electrode providing the possibility of the several reactions to occur in close proximity in the electrolyte 3 (FIG. 2). The working electrode 12 and counter electrode 14 are formed of the same material, such as gold, or other material mentioned above, and are applied to the substrate 15 by thick or thin film technique. A terminal pad 44 is connected to the major extent 45 of the counter electrode 14. The reference electrode 13 is located in a U-shape cut out 46 of the counter electrode and has a terminal pad 47 attached thereto. An advantage to the arrangement shown in FIG. 3 is the opportunity for the several reactions to occur at relatively controlled and desired locations somewhat isolated from relatively wide open discontinuities or spaces between respective electrodes.

Turning to FIG. 4, there is shown a side-by-side arrangement of working, reference and counter electrodes 12, 13, 14. The substrate 15 is not shown in FIGS. 4 through 7, which are simply layout drawings of the respective electrodes. In FIG. 4 the electrodes 12 and 14 are of the fork-like prong type having prongs 50, 51 extending from respective common bases 52, 53 and also having terminal pads 54, 55 extending from the respective bases. The reference electrode 13 is sheet or strip-like and has a terminal pad 56 at the end of the strip or sheet portion 57.

In FIG. 5 is a combination of electrode shapes and arrangement. For example, the working electrode 12 is of the forked prong type surrounded on three sides by a U-shape counter electrode 14. Moreover, the reference electrode 13 is a reverse L-shape surrounding the counter electrode on two sides.

In FIG. 6 the working electrode 12 has a partial circular or arc-shape electrode portion 60. The arcuate portion 60 is circumferentially about central axis 61 and has a terminal pad 62 attached. The counter electrode 14 also has an arcuate portion 63 that is circumferentially located generally concentrically with respect to the portion 60 and the axis 61 allowing clearance space for the extension to the terminal pad 62. Likewise, the reference electrode 13 has an arcuate portion 64 that is generally concentric about the two arcuate portions 60, 63 and axis 61. It will be appreciated, though, that although preferably the arcuate portions 60, 63, 64 are concentric about the axis 61, they need not be exactly so oriented.

Turning briefly to FIG. 7 there is shown a sheet-like working electrode 12 that has a plurality of positionally separated electrode portions 69 exposed through openings 70 in an insulation layer 71 on an electrode sheet 72 for increasing signal-to-noise ratio while decreasing response time, as was mentioned above. The counter electrode 14 is an inverted L-shape, and so is the reference electrode 13, the former bounding the working electrode on two sides and the latter bounding the counter electrode on two sides sandwiching the counter electrode between the working and reference electrodes.

In the several embodiments described above it is to be noted that there is no requirement regarding relative positioning of the several electrodes. For example, in several embodiments the counter electrode is adjacent and separates the reference and working electrodes. If desired, though, the reference and working electrodes may be adjacent. Other electrode configurations also may be used.

Briefly referring to FIG. 8, there is shown a modified embodiment a sensor 10'. Such sensor 10' includes a substrate 15 with three electrodes 12, 13, 14 and appropriate leads, as is illustrated, all located within an electrolyte 3 confined by a barrier 71. The barrier 71 is made of a membrane type material that is selectively permeable to the electrochemically active species intended for detection in the fluid 72. Operation of such a sensor 10' in the sense of use of such a membrane/barrier 71 may be generally as is disclosed in the above mentioned patents.

In FIGS. 9 and 10 is shown a preferred form of working electrode 12' for use in the sensors 10,10'. The working electrode 12' has three sheet-like prongs 80, 81, 83, each formed by a thin or thick film process by which a layer of electrically conductive material 83 is deposited on a substrate 15. A base 41 connects the prongs to each other and to a terminal pad 42. A layer 84 of electrically insulating material is applied over the electrically conductive material 83. Such electrically insulating material has discontinuities therein formed, for example, by an etching process. Such etching process removes selected portions of the insulating material 84 exposing plural discrete working electrode portions 85 and the terminal pad 42.

Since each working electrode portion 85 is relatively small, there will exist a relatively high current density and energy level in proximity thereto helping to induce the desired reduction reaction; the small size and high current density also effect reduction in the time constant for response by the individual working electrode portions 85. Moreover, although the individual currents derived at respective working electrode portions 85 are relatively small, the portions 85 in each prong 81, 82, 83 are connected as in a ladder-like fashion to be in electrical parallel relation. Therefore, the currents are effectively summed in parallel along the respective ladder-like prongs 81, 82, 83, and the currents are further summed at the base 41, as there is current flow with respect to the terminal pad 42. The current sum at the terminal pad, then, is relatively large so as to provide a good signal-to-noise ratio characteristic of the sensor 10 while the response of the sensor is a relatively rapid one.

Using a sensor 10 that is made, for example, in the manner described above using thick or thin film technique, the sensor 10 and sensor system 11 measures the concentration of an electrochemically active species. Accordingly, the sensor would be energized by the circuit 20 to cause reactions at the working and counter electrodes preferably while the voltage between the reference and working electrodes is maintained constant, even though other parameters may vary. The current flowing at the working electrode may be measured by the meter 5 via amplifier 34 (FIG. 2) to obtain information representing concentration of such electrochemically active species.

STATEMENT OF INDUSTRIAL APPLICATION

With the foregoing in mind, it will be appreciated that the invention provides for improvements in electrochemical measurement technology.

We claim:

1. A sensor system for measuring the concentration of an electrochemically active species in an electrolyte, comprising a substrate; a working electrode supported by said substrate; a reference electrode supported by said substrate; a counter electrode supported by said substrate, at least one of said electrodes being formed by thick film or thin film techniques as a layer of electrically conductive material on said substrate; a layer of electrically insulating material on at least a portion of said layer of electrically conductive material, said layer of electrically insulating material having discontinuities to expose individual plural electrode portions; electrical means for providing energy to said electrodes, said electrical means including means for applying voltage potentials to said electrodes and feedback means for controlling the voltage between said reference and counter electrodes thereby to maintain a constant voltage across said working and reference electrodes, such that balanced but reverse ionization reactions of such species respectively occur at said workiing and counter electrodes while essentially no reaction occurs at said reference electrode; and current measuring means for measuring current flow between said working and counter electrodes as a representation of the concentration of such species.

2. The sensor of claim 1, said substrate comprising a flexible polymeric material.

3. The sensor of claim 1, said sensor being of a size having orthogonal surface area dimensions on the order of from about one micron to ten millimeters by about one micron to ten millimeters.

4. The sensor of claim 3, said surface area dimensions being from about one to one hundred microns by about one to one hundred microns.

5. The sensor of claim 3, said surface area dimensions being on the order of, from about one to two millimeters by about one to two millimeters.

6. The sensor of claim 1, said working electrode comprising a material selected from the group of noble metals.

7. The sensor of claim 1, said working electrode comprising a material selected from the group including gold, platinum, silver, and carbon.

8. The sensor of claim 1, said working electrode comprising a material selected from the group including materials that are chemically inert with respect to the electrochemically active species intended for detection using the sensor.

9. The sensor of claim 1, said reference electrode comprising a material selected from the group including silver-silver chloride and mercuric-mercuric chrloride.

10. The sensor of claim 1, 6, 7, or 8, said reference electrode comprising the same material of which said working electrode is comprised.

11. The sensor of claim 1, 6, 7, or 8, said counter electrode comprising the same material of which said working electrode is comprised.

12. The sensor of claim 1, further comprising barrier means for confining in a volume said substrate and electrodes, and an electrolyte within said volume, said barrier means being selectively permeable to such electrochemically active species.

13. The sensor of claim 1, wherein at least one electrode has plural fork-like prong portions extending from a common base.

14. The sensor of claim 1, wherein at least one electrode partly circumscribes a portion of another electrode at boundary areas of said another electrode in plural directions.

15. The sensor of claim 14, said circumscribing electrode being U-shape.

16. The sensor of claim 14, said circumscribing electrode being L-shape or inverted L-shape.

17. The sensor of claim 14, wherein at least two of said electrodes are formed on said substrate in an interdigital arrangement.

18. The sensor of claim 14, wherein each of said electrodes has a partial circular configuration.

19. The sensor of claim 18, wherein said electrodes form respective arcs of respective concentric circles.

20. The sensor of claim 1, wherein each of said electrodes has approximately the same size surface area.

21. The invention of claim 1, wherein such electrochemically active species is oxygen.

22. The invention of claim 1, wherein said reaction at said working electrode is a reduction reaction and said reaction at said counter electrode is an oxidation reaction.

23. The sensor of claim 1, said substrate comprising material selected from the group including plastic, glass, ceramic, alumina and quartz.

24. The sensor of claim 1, wherein all of said electrodes are applied to and supported by a single surface of said substrate, said substrate comprising electrically non-conductive material, and electrical isolation of respective electrodes from each other being by the spacing of such electrodes from each other and by the electrically non-conductive character of said substrate.

25. A method of making a sensor for use in sensing electrochemically active species in an electrolyte, comprising using a thick film or thin film deposition method to apply at least three electrically isolated electrodes to a substrate consisting of a working electrode, counter electrode and reference electrode, and then forming an electrically insulating layer over at least a part of the working electrode with discrete plural discontinuities to expose plural individual electrode portions thereby to provide for relatively high current density and energy level in proximity to such electrode portions for inducing a desired reduction reaction.

26. The method of claim 25, said applying comprising applying such electrodes to an electrically non-conductive substrate of flexible polymeric material.

27. The method of claim 25, said applying comprising applying such electrodes to a common substrate that is less than about ten millimeters by about ten millimeters.

28. The method of claim 27, said applying comprising applying said electrodes to a common substrate that is of a size from about one micron to two millimeters by about one micron to two millimeters.

29. The method of claim 28, said applying comprising applying said electrodes to a common substrate that is less than from about one to fifty microns by about one to fifty microns.

30. A sensor for an electrochemically active species, comprising a substrate, a working electrode supported by said substrate, a reference electrode supported by said substrate, a counter electrode supported by said substrate, at least one of said electrodes including a layer of electrically conductive material on said substrate, and a layer of electrically insulating material on at least a portion of said layer of electrically conductive material, said layer of electrically insulating material having discontinuities to expose individual plural electrode portions.

31. The sense of claim 30, wherein said working electrode includes a layer of electrically conductive material on said substrate having on at least a portion thereof said layer of electrically insulating material having discontinuities to expose individual plural portions of said working electrode.

32. The sensor of claim 31, wherein said working electrode has plural prongs, each joined to sum currents therefrom and at least plural prongs having plural electrode portions exposed at discontinuities in said layer of electrically insulating material.

* * * * *